United States Patent [19]

Salbeck et al.

[11] 4,140,774
[45] Feb. 20, 1979

[54] METHOD OF COMBATING NEMATODES USING S-(AMIDOCARBONYL)-METHYL-O-ALKYL-MONO(DI)THIOPHOSPHORIC ACID ESTER AMIDES

[75] Inventors: Gerhard Salbeck, Hofheim; Hubert Schönowsky, Urberach; Gerhard Hörlein, Frankfurt am Main; Hermann Bieringer, Vockenhausen, Peter Langeluddeke, Diedenbergen, Ludwig Emmel, Bergen-Enkheim; Anna Waltersdorfer, Frankfurt am Main, all of Fed. Rep. of Germany

[73] Assignee: Hoechst Aktiengesellschaft, Frankfurt am Main, Fed. Rep. of Germany

[21] Appl. No.: 764,995

[22] Filed: Feb. 2, 1977

[30] Foreign Application Priority Data

Feb. 4, 1976 [DE] Fed. Rep. of Germany ....... 2604225
Jul. 23, 1976 [DE] Fed. Rep. of Germany ....... 2633159
Apr. 23, 1976 [DE] Fed. Rep. of Germany ....... 2617736

[51] Int. Cl.² ............................ A01N 9/36; C07F 9/24
[52] U.S. Cl. ........................................ 424/211; 71/87; 544/157; 260/943; 424/200; 546/21
[58] Field of Search ................. 260/943; 424/211, 200

[56] References Cited

U.S. PATENT DOCUMENTS

| 3,032,466 | 5/1962 | Schuler | 260/943 X |
| 3,758,644 | 9/1973 | Stolzer et al. | 260/943 X |
| 3,897,520 | 7/1975 | Stolzer et al. | 260/943 |
| 3,907,938 | 9/1975 | Stolzer et al. | 260/943 |

*Primary Examiner*—Anton H. Sutto
*Attorney, Agent, or Firm*—Curtis, Morris & Safford

[57] ABSTRACT

Compounds of the formula

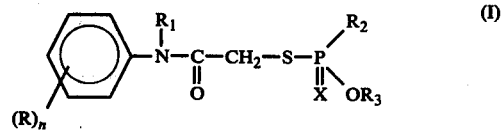

in which R represents halogen, $C_1$–$C_6$-alkyl, $C_1$–$C_3$-haloalkyl, $C_1$–$C_2$ alkoxy, $NO_2$ or $S$-$CH_3$, $R_1$ represents hydrogen or $C_1$–$C_6$-alkyl, $R_2$ represents $C_1$–$C_6$-alkylamino, $C_3$–$C_8$-alkenylamino, N,N-di-($C_1$–$C_6$-alkylamino), $C_5$–$C_8$-cycloalkylamino or a saturated N-heterocycle having from 4 to 8 C-atoms altogether of which 1 or 2 may stand in the side chain and in which one $CH_2$ group of the cycle may be replaced by oxygen or sulfur, $R_3$ represents $C_1$–$C_6$-alkyl, X is oxygen or sulfur and n is zero or a whole number in the range of from 1 to 3 exhibit a good herbicidal effect on some economically important weed grasses and dicotyledonous weeds and simultaneously they have excellent insecticidal and acaricidal properties.

9 Claims, No Drawings

METHOD OF COMBATING NEMATODES USING S-(AMIDOCARBONYL)-METHYL-O-ALKYL-MONO(DI)THIOPHOSPHORIC ACID ESTER AMIDES

This invention relates to compounds of the formula

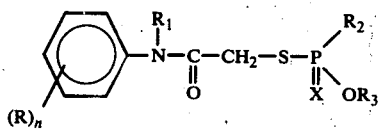

in which
R represents identical or different substituents selected from the group consisting of halogen, $C_1$-$C_6$-alkyl, $C_1$-$C_3$-haloalkyl, $C_1$-$C_2$ alkoxy, $NO_2$ or S-$CH_3$,
$R_1$ represents hydrogen or $C_1$-$C_6$-alkyl,
$R_2$ represents $C_1$-$C_6$-alkylamino, $C_3$-$C_8$-alkenylamino, N,N-di-($C_1$-$C_6$-alkylamino), $C_5$-$C_8$-cycloalkylamino or a saturated N-heterocycle having from 4 to 8 C-atoms altogether of which 1 or 2 may stand in the side chain and in which one $CH_2$ group of the cycle may be replaced by oxygen or sulfur,
$R_3$ represents $C_1$-$C_6$-alkyl,
X is oxygen or sulfur and
n is zero or a whole number in the range of from 1 to 3.

In formula I preferred radicals are:
for
R = F, Cl, Br, $C_1$-$C_4$-alkyl, $CF_3$, $NO_2$,
$R_1$ = H, $C_1$-$C_4$-alkyl
$R_2$ = $C_1$-$C_4$-alkylamino, $C_3$-$C_6$-alkenylamino, N,N-di-($C_1$-$C_4$-alkylamino), $C_5$-$C_8$-cycloalkylamino, morpholino, piperidino, $C_1$-$C_2$-alkylpiperidino and pyrrolidino,
$R_3$ = $C_1$-$C_4$-alkyl.
The compounds of formula I are obtained by reacting (a) compounds of the formula II

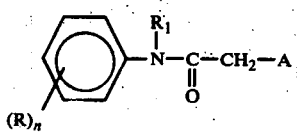

with phosphorus compounds of the formula III

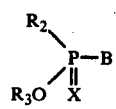

in which formulae one of the radicals A or B stands for halogen, preferably chlorine or bromine, and the other one is the group SY in which Y represents hydrogen or metal cation, optionally in the presence of an acid-binding agent, or b) by first reacting compounds of the formula IV

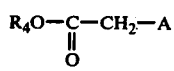

in which $R_4$ preferably represents lower alkyl or phenyl with compounds of the formula III and reacting the intermediates of the formula V

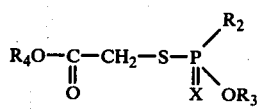

with anilines of the formula VI

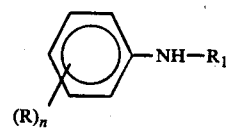

As to (a) the phosphorus compounds of formula III (B = SY) react with chloroacetanilides of formula II (A = Hal) without difficulty at temperatures of 0 to +120° C., preferably of +10 to +80° C.

It proved advisable to perform the reaction in the presence of an inert solvent or diluent such as lower aliphatic ketones, for example acetone or methylethylketone; alkanols, for example methanol, ethanol, or isopropanol; esters, for example acetic acid ethyl ester; nitriles; N-alkylated acid amides, for example dimethyl formamide; ethers, for example dioxane, glycol dimethyl ether or tetrahydrofurane; chlorinated hydrocarbons, for example chloroform or carbon tetrachloride, or water, and mixtures of the aforesaid solvents.

The reaction takes place with exchange of the halogen atom of the chloroacetanilides and, therefore, it is carried out either with the addition of an acid-binding agent or with a salt of the compound of formula III, preferably an alkali metal or ammonium salt. Preferred acid-binding agents are alkali metal hydroxides and carbonates. Tertiary nitrogen bases such as pyridine or triethylamine may likewise be used.

The haloacetic acid anilides of formula II and their preparation are described in literautre.

The SY compounds of formula III are known per se and readily accessible by known methods.

Alternatively, thioglycolic acid anilides of formula II (A = SY) can be reacted with halophosphorus compounds of formula III (B = Hal), in the case of A being SH in the presence of an acid-binding agent. In general approximately stoichiometric amounts of the reactants are used although an excess of the compound of formula II of 5 to 10% may be advantageous.

The reaction is preferably carried out in the presence of an inert solvent as listed above. The reaction temperatures can be varied within a wide range, preferably of from +50 to +120° C. Suitable acid-binding agents are those mentioned above.

The thioglycolic acid anilides of formula II can be prepared by methods described in literature. The halophosphorus compounds of formula III are likewise known and readily accessible according to known methods.

As to (b) the first stage of process b) (reaction of III with IV) corresponds to process a). The intermediate of formula V can be subjected to aminolysis directly without isolation at a temperature in the range of from 0° to 150° C. In this process the reaction temperature depends on the reactivity of the radical $OR_4$; activated esters, for example phenyl esters, reacting at the low temperature.

The compounds of formula I can be used in many fields of plant protection. They exhibit, for example, a good herbicidal activity against a large number of economically important weed grasses with additional effect on dicotyledonous weeds, while they are well tolerated by a number of crop plants, so that they can be used to combat weed grasses and dicotyledonous weeds in many important crops.

The compounds of the invention can be used, for example, to control successfully annual black grass and cleavers in cereals, barnyard grass in maize and foxtail in soya or cotton cultures without damaging the crop plants. In other types of crop plants, for example rice, weed grasses such as barnyard grass and weeds of the sedge family (cyperaceae) are kept under control while the crop plants are left unharmed.

The compounds of the invention have also excellent insecticidal and acaricidal properties. As insecticides and acaricides they have a contact effect as well as an effect on the stomach and, therefore, they can be used to destroy numerous pests including the stages of development in various crop plants without damaging the crop plants. For example, they can be used to control satisfactorily various types of spider mites such as fruit tree red spider (*Metatetranychus ulmi*), citrus spider mite (*Panonychus citri*) and bean spider mite (*Tetranychus urticae*) inclusive of PE resistant strains.

Part of the compounds of formula I also have a good penetrating effect on plants so that pests sitting under the leaves are killed even if only the upper side has been treated.

The compounds of the invention are useful for destroying many insects with sucking and biting mouthparts injurious to crop plants, for example beetles such as the Mexican bean beetle (*Epilachna varivestis*), Colorado beetle (*Leptinotarsa decemlineata*), flower beetle (*Epicometis hirta*), flea beetle (Phyllotreta spp.), strawberry borer (*Coenorrhinus germanicus*), and boll weevil (*Anthonomus grandis*), butterflies and their larvae, such as the Egyptian and old world bollworms (*Earias insulana* and *Heliothis armigera*). leaf rollers, especially codling moth (*Carpocapsa pomonella*), oak leaf roller (*Tortrix viridana*), tordrix moth (*Adoxophyes reticulana*), corn borer (*Ostrinia nubilalis*) and winter moth (*Operophthera brumata*); aphids such as bean aphid (*Doralis fabae*), green peach aphid (*Myzodes persicae*) and cotton aphid (*Aphis gossypii*), bugs such as milk weed bug and cotton stainer (*Oncopeltus fasciatus* and Dysderus spp., especially *fasciatus*); as well as ixodidae in domestic animals, for example *Hyalomma marginatum, Rhipicephalus evertsi, Amblyomma hebraeum* and *Boophilus microplus.*

The compounds of the invention are also suited to combat certain nematode species noxious to plants, for example those of the genera Meloidogyne, Heterodera, Ditylenchus and Aphelenchoides.

In general, the compositions according to the invention contain 2 to 95% by weight of the compounds of formula I. They can be used in the form of wettable powders, emulsifiable concentrates, sprayable solutions, dusts, or granules, in admixture with the usual formulation auxiliaries.

Wettable powders are preparations that can be uniformly dispersed in water and contain, besides the active ingredient, a diluent or an inert substance, a wetting agent, for example polyoxethylated alkylphenols, polyoxethylated oleyl- or stearyl-amines, alkyl- or alkylphenyl-sulfonates, and dispersing agents, for example the sodium salt of lignin-sulfonic acid, of 2,2'-dinaphthylmethane-6,6'-disulfonic acid, dibutylsulfonic acid or sodium oleylmethyltauride.

Emulsifiable concentrates are obtained by dissolving the active ingredient in an organic solvent, for example butanol, cyclohexanone, dimethylformamide, xylene, or aromatic hydrocarbons having a higher boiling point. To obtain suspensions or emulsions in water having good properties, wetting agents as specified above are also added.

Dusting powders are obtained by grinding the active ingredient with finely divided, solid substances, for example talc, natural clays such as kaolin, bentonite, pyrophillite, or diatomaceous earths.

Spraying solutions commercially available as aersol sprays contain the active ingredient dissolved in an organic solvent, and in addition thereto a propellant, for example a mixture of fluorochlorohydrocarbons.

Granules can be produced by atomizing the active ingredient on to an adsorptive, granulated inert material, or by applying concentrates of the active ingredient to the surface of a support, for example sand, kaolinite or a granulated inert material, with the aid of an adhesive, for example polyvinyl alcohol, the sodium salt of polyacrylic acid, or mineral oils. Alternatively, suitable active ingredients may be made into granules, if desired in admixture with fertilizers, in the manner commonly used for the manufacture of granulated fertilizers.

The commercial herbicidal preparations contain varying concentrations of the active ingredients. In wettable powders the concentration of active ingredient varies, for example, from about 10 to 85%, the remainder being the above formulation additives. Emulsion concentrates contain about 10 to 80% of active ingredient, while dusting powders mostly contain 5 to 20% of active ingredient and sprayable solutions about 2 to 20%. In the case of granules, the content of active ingredient partially depends on whether the active ingredient is liquid or solid and on the type of granulation auxiliary or filler used.

For application the commercial concentrates are optionally diluted in usual manner, for example the wettable powder or emulsifiable concentrate with water. Dusts and granulated formulations as well as sprayable solutions are not diluted further with an inert substance before their application.

When used as herbicide the amount applied varies with the external conditions, such as temperature, humidity and the like. In general, about 0.1 to 10 and preferably about 0.15 to 2.5 kg of active ingredient will be used per hectare.

The active ingredients of the invention can be combined with other herbicides, insecticides, acaricides and nematocides. Alternatively, they can be mixed with fertilizers whereby compositions simultaneously having a fertilizing and a pesticidal effect are obtained.

FORMULATION EXAMPLES

EXAMPLE A

A wettable powder which is readily dispersible in water can be obtained by mixing
25 parts by weight of S[N(3-chlorophenyl)-N-methylcarbamoylmethyl]-O-ethyl-isopropylamidothiophosphate as active ingredient 64 parts by weight of kaolin-containing quartz as inert substance
10 parts by weight of the potassium salt of lignin-sulfonic acid
1 part by weight of sodium oleylmethyl tauride as wetting and dispersing agent,
and grinding the mixture obtained in a disk attrition mill.

EXAMPLE B

A dusting powder having good herbicidal properties can be obtained by mixing 10 parts by weight of S[N(3-chlorophenyl)-N-methyl-carbamoylmethyl]-O-ethyl-isopropylamido-thiophosphate as active ingredient
90 parts by weight of talcum as inert substance and grinding the mixture obtained in a cross-beater mill.

EXAMPLE C

An emulsifiable concentrate consists of
15 parts by weight of S[N-(3-chlorophenyl)-N-methylcarbamoylmethyl]-O-ethyl-isopropylamido-thiophosphate as active ingredient
75 parts by weight of cyclohexanone as solvent and
10 parts by weight of nonyl (ethoxy)$_{10}$ phenol as emulsifier.

EXAMPLE D

A granular material consists of about
2 to 15 parts by weight of S[N(3-chlorophenyl)-N-methylcarbamoylmethyl]-O-ethyl-isopropylamido-thiophosphate
and an inert carrier material, for example attapulgite, granulated pumice and quartz sand.

The following examples illustrate the invention.

EXAMPLES OF PREPARATION

General Prescription 0.1 Mol of a chloroacetanilide of formula II (A = Cl) is added at room temperature while stirring to a solution or suspension of 0.01 to 0.11 mol of an ammonium salt of a phosphorus compound of formula III (B = SNH$_4$) in 200 ml of glycol dimethyl ether. The whole is stirred for about 3 to 5 hours at 50° C., the precipitated salt is filtered off with suction, the filtrate is diluted with about 400 ml of benzene, the organic phase is thoroughly washed with water and dried over sodium sulfate. After distillation of the solvent, the compounds of the invention are obtained in the form of oils which partly crystallize on scratching the wall of the container.

Similar yields can be obtained when the process is carried out in lower aliphatic ketones such as acetone or methylethyl ketone, alcohols such as methanol, ethanol or isopropanol, esters such as acetic acid ethyl ester, acetonitrile, dimethyl formamide, ethers such as dioxane or tetrahydrofurane, chlorinated hydrocarbons such as chloroform or carbon tetrachloride, or in water, instead of glycol dimethyl ether. The reaction takes place at a temperature in the range of from 0° C. to the boiling point of the solvent used.

According to the aforesaid prescription the compounds of formula I listed in the following table were prepared and their composition was confirmed by elemental analysis and they were characterized by the refractive index and/or the melting point.

TABLE $$\underset{(R)_n}{\bigcirc}-\underset{\underset{O}{\|}}{\overset{R_1}{\underset{|}{N}}-C-CH_2-S-\overset{R_2}{\underset{\underset{OR_3}{|}}{\overset{\|}{P}}}}$$

| Example No. | (R)$_n$ | R$_1$ | R$_2$ | R$_3$ | X | m.p. or n$_D$ |
|---|---|---|---|---|---|---|
| 1 | H | —CH(CH$_3$)$_2$ | —NH—CH$_3$ | —C$_2$H$_5$ | O | m.p. 67–68° C |
| 2 | 4-F | —CH(CH$_3$)$_2$ | —N(CH$_3$)$_2$ | —C$_2$H$_5$ | O | n$_D^{23}$: 1.5192 |
| 3 | 2-Cl | —CH$_3$ | —NH—CH$_3$ | —C$_2$H$_5$ | O | n$_D^{24}$: 1.5534 |
| 4 | 2-Cl | —CH$_3$ | —NH—CH(CH$_3$)$_2$ | —C$_2$H$_5$ | O | n$_D^{24}$: 1.5473 |
| 5 | 2-Cl | —CH$_3$ | —NH—CH$_2$—CH=CH$_2$ | —C$_2$H$_5$ | O | n$_D^{24}$: 1.5513 |
| 6 | 2-Cl | —CH$_3$ | —NH—C$_4$H$_9$ (n) | —C$_2$H$_5$ | O | n$_D^{24}$: 1.5383 |
| 7 | 3-Cl | —CH$_3$ | —NH—CH$_3$ | —C$_2$H$_5$ | O | n$_D^{24}$: 1.5548 |
| 8 | 3-Cl | —CH$_3$ | —NH—CH(CH$_3$)$_2$ | —C$_2$H$_5$ | O | n$_D^{24}$: 1.5388 |
| 9 | 3-Cl | —CH$_3$ | —NH—CH$_2$—CH=CH$_2$ | —C$_2$H$_5$ | O | n$_D^{24}$: 1.5546 |
| 10 | 3-Cl | —CH$_3$ | —NH—C$_4$H$_9$ (n) | —C$_2$H$_5$ | O | n$_D^{24}$: 1.5410 |
| 11 | 4-Cl | —CH$_3$ | —NH—CH$_3$ | —C$_2$H$_5$ | O | — |
| 12 | 4-Cl | —CH$_3$ | —NH—CH(CH$_3$)$_2$ | —C$_2$H$_5$ | O | n$_D^{24}$: 1.5413 |
| 13 | 4-Cl | —C$_2$H$_5$ | —N(CH$_3$)$_2$ | —C$_2$H$_5$ | O | n$_D^{28}$: 1.5403 |
| 14 | 4-Cl | —C$_4$H$_9$ (sec) | —N(CH$_3$)$_2$ | —C$_2$H$_5$ | O | n$_D^{24}$: 1.5329 |
| 15 | 4-Cl | —C$_4$H$_9$ (sec) | —NH—CH(CH$_3$)$_2$ | —C$_2$H$_5$ | O | n$_D^{24}$: 1.5316 |
| 16 | 4-Br | —CH(CH$_3$)$_2$ | —N(CH$_3$)$_2$ | —C$_2$H$_5$ | O | n$_D^{24}$: 1.5465 |
| 17 | 4-Br | —CH(CH$_3$)$_2$ | —NH—CH(CH$_3$)$_2$ | —C$_2$H$_5$ | O | n$_D^{24}$: 1.5412 |
| 18 | 2,3-Cl | —CH$_3$ | —NH—CH$_3$ | —C$_2$H$_5$ | O | n$_D^{24}$: 1.5585 |
| 19 | 2,3-Cl | —CH$_3$ | —NH—CH(CH$_3$)$_2$ | —C$_2$H$_5$ | O | n$_D^{24}$: 1.5452 |
| 20 | 2,4-Cl | —CH$_3$ | —NH—CH$_3$ | —C$_2$H$_5$ | O | n$_D^{24}$: 1.5604 |
| 21 | 2,4-Cl | —CH$_3$ | —NH—CH(CH$_3$)$_2$ | —C$_2$H$_5$ | O | n$_D^{24}$: 1.5405 |
| 22 | 2,4-Cl | —CH$_3$ | —NH—CH$_2$—CH=CH$_2$ | —C$_2$H$_5$ | O | n$_D^{24}$: 1.5542 |
| 23 | 2,4-Cl | —CH$_3$ | —NH—C$_4$H$_9$ (n) | —C$_2$H$_5$ | O | n$_D^{24}$: 1.5447 |
| 24 | 2,5-Cl | —CH$_3$ | —NH—CH$_3$ | —C$_2$H$_5$ | O | n$_D^{24}$: 1.5645 |
| 25 | 2,5-Cl | —CH$_3$ | —NH—CH(CH$_3$)$_2$ | —C$_2$H$_5$ | O | n$_D^{24}$: 1.5502 |
| 26 | 2,5-Cl | —CH$_3$ | —NH—CH$_2$—CH=CH$_2$ | —C$_2$H$_5$ | O | n$_D^{24}$: 1.5597 |
| 27 | 2,5-Cl | —CH$_3$ | —NH—C$_4$H$_9$ (n) | —C$_2$H$_5$ | O | n$_D^{24}$: 1.5474 |
| 28 | 3,4-Cl | —CH$_3$ | —NH—CH$_3$ | —C$_2$H$_5$ | O | n$_D^{24}$: 1.5620 |
| 29 | 3,4-Cl | —CH$_3$ | —NH—CH(CH$_3$)$_2$ | —C$_2$H$_5$ | O | n$_D^{24}$: 1.5451 |
| 30 | 3,4-Cl | —CH$_3$ | —NH—C$_4$H$_9$ (n) | —C$_2$H$_5$ | O | n$_D^{24}$: 1.5495 |
| 31 | 4-C(CH$_3$)$_2$ | —CH(CH$_3$)$_2$ | —NH—CH$_3$ | —C$_2$H$_5$ | O | n$_D^{24}$: 1.5226 |
| 32 | 4-C(CH$_3$)$_2$ | —CH(CH$_3$)$_2$ | —NH—CH(CH$_3$)$_2$ | —C$_2$H$_5$ | O | n$_D^{24}$: 1.5170 |
| 33 | 3-CF$_3$ | —CH(CH$_3$)$_2$ | —NH—CH$_3$ | —C$_2$H$_5$ | O | n$_D^{24}$: 1.4980 |
| 34 | 3-CF$_3$ | —CH(CH$_3$)$_2$ | —N(CH$_3$)$_2$ | —C$_2$H$_5$ | O | n$_D^{26}$: 1.4935 |
| 35 | 3-CF$_3$ | —CH(CH$_3$)$_2$ | —NH—CH(CH$_3$)$_2$ | —C$_2$H$_5$ | O | n$_D^{24}$: 1.4953 |
| 36 | 3-CF$_3$ | —C$_4$H$_9$ (sec) | —NH—CH$_3$ | —C$_2$H$_5$ | O | n$_D^{24}$: 1.4994 |
| 37 | 3-CF$_3$ | —C$_4$H$_9$ (sec) | —N(CH$_3$)$_2$ | —C$_2$H$_5$ | O | n$_D^{24}$: 1.4930 |
| 38 | 3-CF$_3$ | —C$_4$H$_9$ (sec) | —NH—CH(CH$_3$)$_2$ | —C$_2$H$_5$ | O | n$_D^{24}$: 1.4953 |

TABLE-continued $$\underset{(R)_n}{\text{Ar}}-\underset{R_1}{N}-\underset{O}{\overset{\|}{C}}-CH_2-S-\underset{X}{\overset{R_2}{\underset{\|}{P}}}-OR_3$$

| Example No. | (R)$_n$ | R$_1$ | R$_2$ | R$_3$ | X | m.p. or n$_D$ |
|---|---|---|---|---|---|---|
| 39 | 3-CF$_3$ | —C$_4$H$_9$ (sec) | —NH—CH$_2$—CH=CH$_2$ | —C$_2$H$_5$ | O | n$_D^{24}$: 1.5047 |
| 40 | 4-Cl | —CH(CH$_3$)$_2$ | —NH—CH$_3$ | —CH$_3$ | O | — |
| 41 | 2-F | —CH(CH$_3$)$_2$ | —NH—CH(CH$_3$)$_2$ | —C$_2$H$_5$ | O | n$_D^{24}$: 1.5171 |
| 42 | H | H | —NH—C$_3$H$_7$ iso | —C$_2$H$_5$ | O | n$_D^{30}$: 1.5666 |
| 43 | H | H | | —C$_2$H$_5$ | O | m.p. 90–93° C |
| 44 | H | H | —NH—C$_6$H$_{11}$ | —C$_2$H$_5$ | O | |
| 45 | H | H | —N(morpholino) | —C$_2$H$_5$ | O | n$_D^{29}$: 1.5568 |
| 46 | H | CH$_3$ | —N(morpholino) | —C$_2$H$_5$ | O | — |
| 47 | 3-CH$_3$ | C$_3$H$_7$-iso | —NH—C$_4$H$_9$n | —C$_2$H$_5$ | O | n$_D^{29}$: 1.5236 |
| 48 | 4-CH$_3$ | —CH(CH$_3$)$_2$ | —NH—C$_4$H$_9$n | —C$_2$H$_5$ | O | m.p. 59–64° C |
| 49 | 4-CH$_3$ | —CH(CH$_3$)$_2$ | —NH—CH$_2$—CH=CH$_2$ | —C$_2$H$_5$ | O | n$_D^{29}$: 1.5362 |
| 50 | 2-CH$_3$ | —CH(CH$_3$)$_2$ | —NH—C$_3$H$_7$-iso | —C$_2$H$_5$ | O | n$_D^{32}$: 1.5255 |
| 51 | 2-CH$_3$ | —CH(CH$_3$)$_2$ | —NH—CH$_2$—CH=CH$_2$ | —C$_2$H$_5$ | O | n$_D^{29}$: 1.5375 |
| 52 | 2,5-Cl | —CH$_3$ | —NH—CH(CH$_3$)$_2$ | —C$_2$H$_5$ | S | n$_D^{28}$: 1.5647 |
| 53 | 4-Cl | —CH(CH$_3$)$_2$ | —NH—C$_6$H$_{11}$ | —C$_2$H$_5$ | O | — |
| 54 | 3-Cl | —CH$_3$ | '' | —C$_2$H$_5$ | O | n$_D^{30}$: 1.5475 |
| 55 | 3-Cl | —CH$_3$ | —N(piperidino) | —C$_2$H$_5$ | O | n$_D^{30}$: 1.5540 |
| 56 | 2,4-Cl | —CH$_3$ | —NH—CH$_3$ | —C$_2$H$_5$ | O | n$_D^{24}$: 1.5604 |
| 57 | H | —CH$_3$ | —NHC$_3$H$_7$-iso | —C$_2$H$_5$ | O | n$_D^{27}$: 1.5472 |
| 58 | 3-CH$_3$ | —CH(CH$_3$)$_2$ | —NHC$_3$H$_7$-iso | —C$_2$H$_5$ | O | n$_D^{32}$: 1.5188 |
| 59 | 3-CH$_3$ | —CH(CH$_3$)$_2$ | —NH—CH$_2$—CH=CH$_2$ | —C$_2$H$_5$ | O | n$_D^{30}$: 1.5343 |
| 60 | 3-CH$_3$ | —CH(CH$_3$)$_2$ | —N(morpholino) | —C$_2$H$_5$ | O | n$_D^{32}$: 1.5350 |
| 61 | 4-CH$_3$ | —CH(CH$_3$)$_2$ | —N(morpholino) | —C$_2$H$_5$ | O | n$_D^{32}$: 1.5343 |
| 62 | 4-CH$_3$ | —CH(CH$_3$)$_2$ | —NHC$_3$H$_7$-iso | —C$_2$H$_5$ | O | m.p. 69–71° C |
| 63 | 2-CH$_3$ | —CH(CH$_3$)$_2$ | —NHC$_4$H$_9$-iso | —C$_2$H$_5$ | O | n$_D^{32}$: 1.5257 |
| 64 | 2-CH$_3$ | —CH(CH$_3$)$_2$ | —N(morpholino) | —C$_2$H$_5$ | O | n$_D^{32}$: 1.5337 |
| 65 | 3-Cl | —CH$_3$ | —N(morpholino) | —C$_2$H$_5$ | O | n$_D^{27}$: 1.555 |
| 66 | 2,4-Cl | —CH(CH$_3$)$_2$ | —NH—C$_6$H$_{11}$ | —C$_2$H$_5$ | O | m.p. 90–94° C |
| 67 | 2,4-Cl | —CH$_3$ | —N(morpholino) | —C$_2$H$_5$ | O | n$_D^{27}$: 1.5551 |
| 68 | 3,4-Cl | —CH(CH$_3$)$_2$ | —NHC$_4$H$_9$-n | —C$_2$H$_5$ | O | n$_D^{29}$: 1.5402 |
| 69 | 3,4-Cl | —CH(CH$_3$)$_2$ | —NHC$_3$H$_7$-iso | —C$_2$H$_5$ | O | n$_D^{31}$: 1.5419 |
| 70 | 3-Cl | —CH(CH$_3$)$_2$ | —NHC$_3$H$_7$-iso | —C$_2$H$_5$ | O | n$_D^{31}$: 1.5350 |
| 71 | 4-Br | —CH(CH$_3$)$_2$ | —NHC$_3$H$_7$-iso | —C$_2$H$_5$ | O | m.p. 85–86° C |
| 72 | 2,5-Cl | —CH(CH$_3$)$_2$ | —NHC$_3$H$_7$-iso | —C$_2$H$_5$ | O | m.p. 103–105° C |
| 73 | 4-NO$_2$ | —CH(CH$_3$)$_2$ | —NHC$_3$H$_7$-iso | —C$_2$H$_5$ | O | m.p. 46–52° C |
| 74 | 4-NO$_2$ | —CH(CH$_3$)$_2$ | —NHC$_4$H$_9$-n | —C$_2$H$_5$ | O | m.p. 69–71° C |

TABLE-continued $$\text{(R)}_n\text{-C}_6\text{H}_4\text{-N(R}_1\text{)-C(O)-CH}_2\text{-S-P(R}_2\text{)(X)(OR}_3\text{)}$$

| Example No. | (R)$_n$ | R$_1$ | R$_2$ | R$_3$ | X | m.p. or n$_D$ |
|---|---|---|---|---|---|---|
| 75 | 4-NO$_2$ | —CH(CH$_3$)$_2$ | —NH—CH$_2$—CH=CH$_2$ | —C$_2$H$_5$ | O | n$_D^{32}$: 1.5549 |
| 76 | 4-NO$_2$ | —CH(CH$_3$)$_2$ | —N(piperidine) | —C$_2$H$_5$ | O | n$_D^{32}$: 1.5483 |
| 77 | 4-SCH$_3$ | —CH(CH$_3$)$_2$ | —NHC$_3$H$_7$-iso | —C$_2$H$_5$ | O | m.p. 81–84° C |
| 78 | 2,4-Cl | —CH$_3$ | —NHCH(CH$_3$)$_2$ | —C$_2$H$_5$ | O | n$_D^{24}$: 1.5405 |
| 79 | 2,4-Cl | —CH$_3$ | —NH—CH$_2$—CH=CH$_2$ | —C$_2$H$_5$ | O | n$_D^{24}$: 1.5542 |
| 80 | 3-CH$_3$ | —CH(CH$_3$)$_2$ | —NH-Cyclohexyl | —C$_2$H$_5$ | O | n$_D^{28}$: 1.5370 |
| 81 | 3-CH$_3$ | —CH(CH$_3$)$_2$ | —N(piperidine) | —C$_2$H$_5$ | O | n$_D^{31}$: 1.5347 |
| 82 | 4-CH$_3$ | —CH(CH$_3$)$_2$ | —NH-Cyclohexyl | —C$_2$H$_5$ | O | m.p. 74–75° C |
| 83 | 4-CH$_3$ | —CH(CH$_3$)$_2$ | —N(piperidine) | —C$_2$H$_5$ | O | n$_D^{31}$: 1.5340 |
| 84 | 4-SCH$_3$ | —CH(CH$_3$)$_2$ | —NHC$_4$H$_9$-n | —C$_2$H$_5$ | O | m.p. 65–67° C |
| 85 | 4-NO$_2$ | —CH(CH$_3$)$_2$ | —N(morpholine) | —C$_2$H$_5$ | O | n$_D^{24}$: 1.5608 |
| 86 | 4-NO$_2$ | —C$_2$H$_5$ | —NHC$_4$H$_9$-n | —C$_2$H$_5$ | O | m.p. 75–76° C |
| 87 | 4-NO$_2$ | —C$_2$H$_5$ | —N(morpholine) | —C$_2$H$_5$ | O | n$_D^{27}$: 1.5620 |
| 88 | 3-NO$_2$ | —CH$_3$ | —NHC$_3$H$_7$-iso | —C$_2$H$_5$ | O | n$_D^{27}$: 1.5519 |
| 89 | 3-NO$_2$ | —CH$_3$ | —NH—CH$_2$—CH=CH$_2$ | —C$_2$H$_5$ | O | m.p. 86–87° C |
| 90 | 3-NO$_2$ | —CH$_3$ | —N(morpholine) | —C$_2$H$_5$ | O | n$_D^{27}$: 1.5622 |
| 91 | 3-Cl | —CH$_3$ | —NHC$_3$H$_7$-iso | —C$_2$H$_5$ | S | n$_D^{28}$: 1.5752 |
| 92 | 2,5-Cl | —CH$_3$ | —NHC$_3$H$_7$-iso | —C$_2$H$_5$ | S | n$_D^{28}$: 1.5647 |
| 93 | 2,4,6-Cl | H | —NHC$_3$H$_7$-iso | —C$_2$H$_5$ | O | n$_D^{23}$: 1.561 |
| 94 | 2,4,6-Cl | H | —NH—CH$_2$—CH=CH$_2$ | —C$_2$H$_5$ | O | m.p. 55–57° C |
| 95 | 2,4,6-Cl | H | —NHC$_4$H$_9$-n | —C$_2$H$_5$ | O | m.p. 82–85° C |
| 96 | 3,4,5-Cl | H | —NHC$_3$H$_7$-iso | —C$_2$H$_5$ | O | m.p. 168–171° C |
| 97 | 3,4,5-Cl | H | —NH—CH$_2$—CH=CH$_2$ | —C$_2$H$_5$ | O | m.p. 119–121° C |
| 98 | 3,4,5-Cl | H | —NHC$_4$H$_9$-n | —C$_2$H$_5$ | O | m.p. 93–96° C |
| 99 | 3,4,5-Cl | —CH$_3$ | —NHC$_3$H$_7$-iso | —C$_2$H$_5$ | O | m.p. 84–87° C |
| 100 | 3,4,5-Cl | —CH$_3$ | —NHC$_4$H$_9$-n | —C$_2$H$_5$ | O | n$_D^{23}$: 1.5594 |
| 101 | 2-CH$_3$ | —CH(CH$_3$)$_2$ | —N(piperidine) | —C$_2$H$_5$ | O | n$_D^{28}$: 1.5360 |
| 102 | H | —CH(CH$_3$)$_2$ | —NH—C$_3$H$_7$(n) | —C$_2$H$_5$ | S | m.p. 76–78° C |

BIOLOGICAL EXAMPLES

Biological examination of the compounds of the invention revealed that they had a good herbicidal effect against a wide range of economically important weed grasses such as Lolium, Poa, Setaria and Echinochloa combined with an additional effect on dicotyledonous weeds. When applied in herbicidally active amounts, the compounds of the invention did no harm to many important crop plants so that they can be used to combat grassy and dicotyledonous weeds therein.

EXAMPLE I (Pre-emergence trial)

The compounds of the invention were sprayed in different concentrations on the soil in pots into which seeds of important weeds had been sown. After the treatment the pots were placed in a greenhouse and the effect of the compounds was evaluated after different periods after application according to the usual EWRC scheme.

Evaluation scheme according to Bolle (Nachrichtenblatt des deutschen Pflanzenschutzdienstes 16, 1964, pages 92 to 94).

| number | degree of damage in % weeds | | crop plants | |
|---|---|---|---|---|
| 1 | 100 | | 0 | |
| 2 | 97,5 to | <100 | >0 to | 2,5 |
| 3 | 95 to | <97.5 | >2,5 to | 5 |
| 4 | 90 to | <95 | >5 to | 10 |
| 5 | 85 to | <90 | >10 to | 15 |
| 6 | 75 to | <85 | >15 to | 25 |
| 7 | 65 to | <75 | >25 to | 35 |

-continued

| number | degree of damage in % | | | |
|---|---|---|---|---|
| | weeds | | crop plants | |
| 8 | 32.5 to | <65 | >35 to | 67.5 |
| 9 | 0 to | <32.5 | >67.5 to | 100 |

The final evaluation about 4 weeks after treatment indicated that the compounds of the invention had a very good herbicidal effect against many economically important weed grasses and also combated dicotyledonous weeds well when applied in amounts usual in the field. As comparative compounds the following phosphoric acid esters were used:

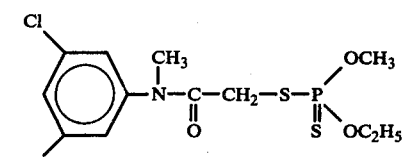
A

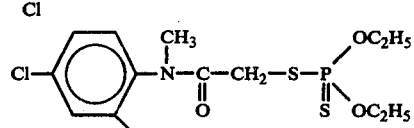
B

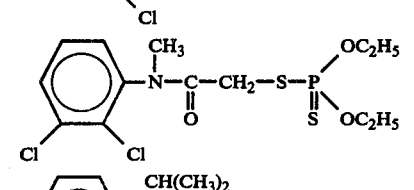
C

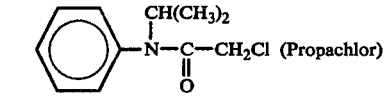
D

In the table the abbreviation AS means active substance.

TABLE Ia

| Compound of Ex. No. | kg As /ha | Pre-emergence effect on weed grasses | | | | | |
|---|---|---|---|---|---|---|---|
| | | Alope-curus | setaria | Poa annua | Poa tri-vialis | Lolium | Echino-chloa |
| 8 | 2.5 | 2 | 1 | 1 | 1 | 1 | 1 |
| | 0.6 | 7 | 5 | 4 | 1 | 7 | 6 |
| 25 | 2.5 | 1 | 1 | 1 | 1 | 1 | 1 |
| | 0.6 | 6 | 5 | 2 | 1 | 2 | 1 |
| 26 | 2.5 | 1 | 1 | 1 | 1 | 1 | 1 |
| | 0.6 | 5 | 2 | 1 | 1 | 1 | 2 |
| 28 | 2.5 | 2 | 1 | 1 | 1 | 1 | 1 |
| | 0.6 | 8 | 1 | 3 | 3 | 7 | 2 |
| A | 2.5 | 4 | 1 | 1 | 1 | 8 | 1 |
| | 0.6 | 8 | 2 | 2 | 3 | 9 | 1 |
| B | 2.5 | 4 | 3 | 1 | 1 | 8 | 4 |

TABLE Ia-continued

| Compound of Ex. No. | kg As /ha | Pre-emergence effect on weed grasses | | | | | |
|---|---|---|---|---|---|---|---|
| | | Alope-curus | setaria | Poa annua | Poa tri-vialis | Lolium | Echino-chloa |
| | 0.6 | 8 | 7 | 8 | 5 | 9 | 8 |
| C | 2.5 | 2 | 1 | 1 | 1 | 8 | 1 |
| | 0.6 | 8 | 8 | 8 | 1 | 9 | 7 |
| D | 2.5 | 9 | 2 | 6 | 4 | 8 | 3 |
| | 0.6 | 9 | 8 | 9 | 7 | 9 | 8 |
| 2 | 2.5 | 1 | 1 | 1 | 1 | 1 | 1 |
| 9 | 2.5 | 1 | 1 | 1 | 1 | 1 | 1 |
| 54 | 2.5 | 1 | 1 | 1 | 1 | 1 | 1 |
| 55 | 2.5 | 1 | 1 | 1 | 1 | 1 | 1 |
| 10 | 2.5 | 1 | 1 | 1 | 1 | 1 | 1 |
| 17 | 2.5 | 1 | 1 | 1 | 1 | 1 | 1 |
| 66 | 2.5 | 1 | 1 | 1 | 1 | 1 | 1 |
| 24 | 2.5 | 1 | 1 | 1 | 1 | 1 | 1 |
| 25 | 2.5 | 1 | 1 | 1 | 1 | 1 | 1 |
| 27 | 2.5 | 1 | 1 | 1 | 1 | 1 | 1 |
| 68 | 2.5 | 1 | 1 | 1 | 1 | 1 | 1 |
| 69 | 2.5 | 1 | 1 | 1 | 1 | 1 | 1 |
| 62 | 2.5 | 1 | 1 | 1 | 1 | 1 | 1 |
| 73 | 2.5 | 1 | 1 | 1 | 1 | 1 | 1 |
| 74 | 2.5 | 1 | 1 | 1 | 1 | 1 | 1 |
| 75 | 2.5 | 1 | 1 | 1 | 1 | 1 | 1 |
| 88 | 2.5 | 1 | 1 | 1 | 1 | 1 | 1 |
| 89 | 2.5 | 1 | 1 | 1 | 1 | 1 | 1 |
| 91 | 2.5 | 1 | 1 | 1 | 1 | 1 | 1 |

TABLE Ib

| compound of Example No. | kg AS/ha | Pre-emergence effect on dicotyledonous weeds | | | | |
|---|---|---|---|---|---|---|
| | | Gali-ium | Cheno-podium | Chrysan-themum | Stell-aria | Amar-anthus |
| 8 | 2.5 | 8 | 6 | 1 | 1 | 1 |
| | 0.6 | 9 | 8 | 8 | 8 | 5 |
| 25 | 2.5 | 4 | 4 | 1 | 1 | 1 |
| | 0.6 | 7 | 8 | 6 | 9 | 5 |
| 26 | 2.5 | 1 | 1 | 2 | 1 | 1 |
| | 0.6 | 8 | 6 | 8 | 8 | 2 |
| 28 | 2.5 | 8 | 2 | 5 | 1 | 1 |
| | 0.6 | 9 | 7 | 9 | 8 | 8 |
| A | 2.5 | 9 | 8 | 8 | 9 | 9 |
| | 0.6 | 9 | 9 | 9 | 9 | 9 |
| B | 2.5 | 8 | 8 | 8 | 3 | 7 |
| | 0.6 | 9 | 9 | 9 | 8 | 9 |
| C | 2.5 | 7 | 8 | 8 | 8 | 6 |
| | 0.6 | 9 | 9 | 9 | 9 | 9 |

EXAMPLE II (Pre-emergence trial)

In a manner analogous to that described in Example I, compounds of the invention were tested as to their effect in crop plants. The results listed in Table II show that concentrations of from 0.6 to 2.5 kg/hectare of active substance did no harm to numerous important agricultural and horticultural crops. Hence, the compounds can be used to combat for example Alopecurus and Galium in cereals, Echinochloa in maize and Setaria in soybean or cotton.

TABLE II

| Example No. | kg/ha | Effect on crop plants in pre-emergence trial | | | | | | | | | | |
|---|---|---|---|---|---|---|---|---|---|---|---|---|
| | | Wheat | Rice | Sugar beet | Rape | Cucum-ber | Soy bean | Bean | cotton | Tomato | Carrot | Maize |
| 8 | 2.5 | 2 | 1 | 1 | 1 | 1 | 1 | 1 | 1 | 1 | 1 | 2 |
| | 0.6 | 1 | 1 | 1 | 1 | 1 | 1 | 1 | 1 | 1 | 1 | 1 |
| 25 | 2.5 | 3 | 2 | 1 | 1 | 1 | 1 | 1 | 1 | 1 | 1 | 3 |
| | 0.6 | 1 | 1 | 1 | 1 | 1 | 1 | 1 | 1 | 1 | 1 | 2 |
| 26 | 2.5 | 4 | 3 | 1 | 1 | 1 | 1 | 1 | 1 | 1 | 1 | 3 |
| | 0.6 | 1 | 1 | 1 | 1 | 1 | 1 | 1 | 1 | 1 | 1 | 2 |
| 28 | 2.5 | 2 | 2 | 1 | 1 | 1 | 1 | 1 | 1 | 1 | 1 | 3 |
| | 0.6 | 1 | 1 | 1 | 1 | 1 | 1 | 1 | 1 | 1 | 1 | 1 |

EXAMPLE III

The following trial was carried out to prove the effect on aphids.

Horse beans (*Vicia faba*) infested with black bean aphids (*Doralis fabae*) were sprayed to the drip-off with aqueous suspensions of wettable powders containing the active substance in the concentrations indicated in Table III. The plants were kept in the greenhouse at 22° C.

Table III

| Compound of Example No. | wt.% AS in spray liquor | % destruction after 3 days |
| --- | --- | --- |
| 37 | 0.0125 | 100 |
|  | 0.006 | 70 |
| 13 | 0.003 | 100 |
| 14 | 0.0125 | 90 |
| 2 | 0.006 | 100 |
|  | 0.003 | 90 |
| 16 | 0.006 | 100 |
|  | 0.003 | 50 |
| 1 | 0.0125 | 100 |
|  | 0.006 | 80 |
| 22 | 0.0125 | 100 |
| 32 | 0.025 | 100 |
| 36 | 0.025 | 100 |
| 41 | 0.006 | 100 |
| 42 | 0.003 | 100 |
| 46 | 0.05 | 100 |
| 49 | 0.025 | 100 |
| 50 | 0.006 | 100 |
| 51 | 0.006 | 100 |
| 52 | 0.025 | 100 |
| 56 | 0.0125 | 100 |
| 58 | 0.0125 | 100 |
| 59 | 0.0125 | 100 |
| 63 | 0.006 | 100 |
| 69 | 0.0125 | 100 |
| 70 | 0.006 | 100 |
| 71 | 0.0125 | 100 |
| 73 | 0.025 | 100 |
| 75 | 0.0125 | 100 |
| 79 | 0.0125 | 100 |
| 86 | 0.0125 | 100 |
| 88 | 0.0125 | 100 |
| 91 | 0.003 | 100 |
| 92 | 0.025 | 100 |
| 93 | 0.0125 | 100 |
| 99 | 0.0125 | 100 |
| 100 | 0.025 | 100 |

When tested under equal conditions, the compounds of Example 18, 4, 5, 7, 8, 9, 11, 12, 17, 20, 21, 25, 27, 29, 30, 35, and 39 exhibited the same effect.

EXAMPLE IV

A dust formulation was mixed with soil infested with nematodes of the genus Meloidogyne incognita. The soil was filled in pots in which tomatoes were then planted. After 4 weeks at 25° C. and a relatively humidity of 70%, the number of galls was counted and the following evaluation scheme was set up:

| galls per plant | evaluation number |
| --- | --- |
| 0 | 1 |
| 1–2 | 2 |
| 3–5 | 3 |
| 6–10 | 4 |
| 11–20 | 5 |
| 21–40 | 6 |
| 41–80 | 7 |
| 81–150 | 8 |
| 150 | 9 |

The effectiveness of the tested compounds is indicated in the following table IV.

Table IV

| Compound of Example No. | amount of AS kg/hectare | evaluation number |
| --- | --- | --- |
| 1 | 20 | 1 |
|  | 10 | 1 |
|  | 5 | 2 |
| 35 | 20 | 1 |
|  | 10 | 3 |
| 2 | 40 | 1 |
|  | 20 | 2 |
|  | 10 | 4 |
| 21 | 5 | 1 |
| 12 | 5 | 2 |
| 8 | 5 | 1 |
| 25 | 5 | 1 |
| 7 | 10 | 1 |
| 19 | 10 | 1 |
|  | 5 | 2 |
| 18 | 10 | 1 |
| 4 | 20 | 1 |
|  | 10 | 1 |
| 5 | 20 | 1 |
|  | 10 | 3 |
| 6 | 20 | 1 |
|  | 10 | 3 |
| 20 | 20 | 2 |
| 29 | 20 | 1 |
| 33 | 20 | 1 |
| 28 | 40 | 1 |
|  | 20 | 2 |
| 102 | 10 | 1 |
| 24 | 10 | 1 |
|  | 5 | 2 |
| 57 | 2 | 1 |
| 70 | 10 | 2 |
| 72 | 10 | 1 |
| 77 | 20 | 1 |
| 78 | 20 | 1 |
| untreated control |  | 9 |

EXAMPLE V

Milkweed bugs (*Oncopeltus fasciatus*) were sprayed to the drip off with aqueous suspensions of wettable powders containing the amounts of active substance of the respective compounds indicated in Table V. The bugs were then placed in receptacles with covers permeable to air and kept at room temperature. The results obtained are indicated in Table V.

Table V

| Compound of Example No. | wt.% AS in spray liquor | % destruction after 5 days |
| --- | --- | --- |
| 5 | 0.0125 | 100 |
|  | 0.006 | 30 |
| 10 | 0.0125 | 100 |
|  | 0.006 | 70 |
| 21 | 0.0125 | 100 |
|  | 0.006 | 50 |
| 25 | 0.0125 | 100 |
|  | 0.006 | 20 |
| 27 | 0.015 | 100 |
|  | 0.006 | 60 |
| 6 | 0.025 | 100 |
|  | 0.0125 | 85 |
| 8 | 0.006 | 100 |
|  | 0.003 | 60 |
| 12 | 0.025 | 100 |
|  | 0.0125 | 80 |
| 23 | 0.025 | 100 |
|  | 0.0125 | 70 |
| 30 | 0.025 | 100 |
|  | 0.0125 | 70 |
| 48 | 0.025 | 100 |
| 51 | 0.025 | 100 |
| 55 | 0.025 | 100 |
| 54 | 0.025 | 100 |
| 62 | 0.025 | 100 |
| 68 | 0.025 | 100 |
| 69 | 0.025 | 100 |
| 86 | 0.025 | 100 |
| 88 | 0.0125 | 100 |
| 89 | 0.0125 | 100 |
| 91 | 0.006 | 100 |
| 100 | 0.025 | 100 |

What is claimed is:

1. A method of combating nematodes which comprises treating nematode-infested soil or plants with a nematodicidally effective amount of a compound of the formula

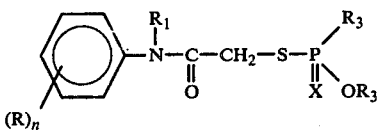

in which
R represents identical or different substituents selected from the group consisting of halogen, $C_1-C_6$-alkyl, $C_1-C_3$-haloalkyl, $C_1-C_2$-alkoxy, $NO_2$ or $S-CH_3$,
$R_1$ represents $C_1-C_6$-alkyl,
$R_2$ represents $C_1-C_6$-alkylamino, $C_3-C_8$-alkenylamino, N,N-di-($C_1-C_6$-alkylamino), $C_5-C_8$-cycloalkylamino or a saturated N-heterocycle selected from morpholino and piperidino,
$R_3$ represents $C_1-C_6$-alkyl,
X is oxygen or sulfur and
n is zero or a whole number in the range of from 1 to 3.

2. A nematodicidal composition consisting essentially of an inert carrier and a nematodicidally effective compound of the formula

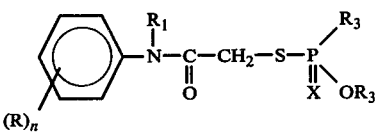

in which
R represents identical or different substituents selected from the group consisting of halogen, $C_1-C_6$-alkyl, $C_1-C_3$-haloalkyl, $C_1-C_2$-alkoxy, $NO_2$ or $S-CH_3$,
$R_1$ represents $C_1-C_6$-alkyl,
$R_2$ represents $C_1-C_6$-alkylamino, $C_3-C_8$-alkenylamino, N,N-di-($C_1-C_6$-alkylamino), $C_5-C_8$-cycloalkylamino or a saturated N-heterocycle selected from morpholino and piperidino,
$R_3$ represents $C_1-C_6$-alkyl,
X is oxygen or sulfur and
n is zero or a whole number in the range of from 1 to 3.

3. A nematodicidal composition according to claim 2 wherein the nematodicidally effective compound is of the formula

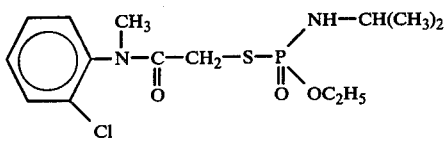

4. A nematodicidal composition according to claim 2 wherein the nematodicidally effective compound is of the formula

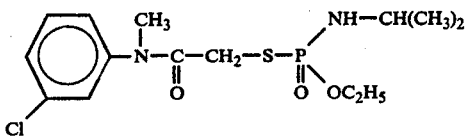

5. A nematodicidal composition according to claim 2 wherein the nematodicidally effective compound is of the formula

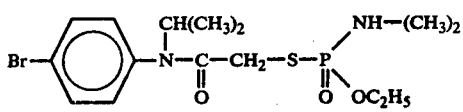

6. A nematodicidal composition according to claim 2 wherein the nematodicidally effective compound is of the formula

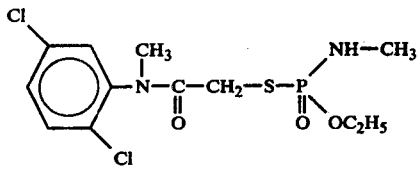

7. A nematodicidal composition according to claim 2 wherein the nematodicidally effective compound is of the formula

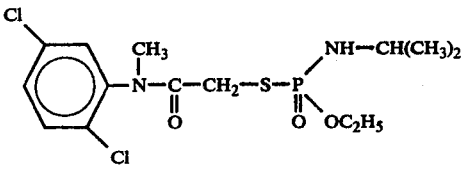

8. A nematodicidal composition according to claim 2 wherein the nematodicidally effective compound is of the formula

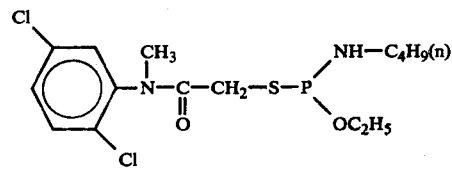

9. A nematodicidal composition according to claim 2 wherein the nematodicidally effective compound is of the formula

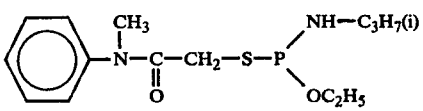

* * * * *